United States Patent
Ryu et al.

(10) Patent No.: US 9,468,414 B2
(45) Date of Patent: Oct. 18, 2016

(54) IMAGING SYSTEM

(71) Applicant: CANON KABUSHIKI KAISHA, Tokyo (JP)

(72) Inventors: Takuya Ryu, Kokubunji (JP); Toshio Kameshima, Kumagaya (JP); Tomoyuki Yagi, Honjo (JP); Katsuro Takenaka, Honjo (JP); Sho Sato, Saitama (JP); Atsushi Iwashita, Saitama (JP); Eriko Sato, Tokyo (JP); Hideyuki Okada, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 146 days.

(21) Appl. No.: 14/211,970

(22) Filed: Mar. 14, 2014

(65) Prior Publication Data

US 2014/0285689 A1 Sep. 25, 2014

(30) Foreign Application Priority Data

Mar. 19, 2013 (JP) .................... 2013-056877

(51) Int. Cl.
*A61B 6/00* (2006.01)
*G01T 7/00* (2006.01)
(Continued)

(52) U.S. Cl.
CPC ........... *A61B 6/5258* (2013.01); *A61B 6/5205* (2013.01); *G06T 5/002* (2013.01);
(Continued)

(58) Field of Classification Search
CPC .... A61B 6/42; A61B 6/5205; A61B 6/5258; A61B 6/585; A61B 6/00; A61B 6/025; A61B 6/0421; A61B 6/4233; A61B 6/502; A61B 6/52; A61B 6/58; A61B 6/582; G01T 1/2018; G01T 7/005; H04N 5/2173; H04N 5/32; H04N 5/357; H04N 5/3651; H04N 5/347; H04N 5/367; H04N 5/378; H04N 5/232; H04N 5/343; H04N 5/3454; H04N 5/3658; H04N 5/3742; H04N 5/361; H04N 19/1883; H04N 19/63; H04N 1/407; H04N 1/4072; H04N 1/4092; H04N 5/2178; H04N 5/23238; H04N 5/2351; H04N 5/243; H04N 5/325; H04N 5/355; H04N 5/3559; H04N 5/37452; G06T 5/00; G06T 5/001; G06T 5/002; G06T 5/50
USPC ........................................................ 378/98.8
See application file for complete search history.

(56) References Cited

U.S. PATENT DOCUMENTS 6,731,720 B2   5/2004   Matsuura
7,342,221 B2   3/2008   Takenaka et al.
(Continued)

FOREIGN PATENT DOCUMENTS

JP           3894534 B2     12/2006

OTHER PUBLICATIONS

U.S. Appl. No. 14/292,230, filed May 30, 2014.

*Primary Examiner* — Anastasia Midkiff
(74) *Attorney, Agent, or Firm* — Fitzpatrick, Cella, Harper & Scinto

(57) ABSTRACT

An imaging system comprises: a plurality of pixels each for converting light, converted from radiation by a conversion unit, into an electrical signal; an extracting unit that extracts, based on an image formed based on output signals from the pixels, a pixel with noise generated by the radiation that has transmitted through the conversion unit to arrive at the pixels; and a correcting unit that performs correction to remove the noise with respect to an output signal from the extracted pixel, wherein the extracting unit extracts the pixel with the noise by performing division between first and second images, the first image being formed based on the output signals from the pixels in accordance with the radiation to the conversion unit during a first period, the second image being formed based on these output signals in accordance with that radiation during a second period after the first period.

9 Claims, 12 Drawing Sheets

(51) Int. Cl.
  G06T 5/50 (2006.01)
  H04N 5/32 (2006.01)
  H04N 5/357 (2011.01)
  G06T 5/00 (2006.01)
  H04N 5/325 (2006.01)
  H04N 5/347 (2011.01)
  H04N 5/378 (2011.01)
  G01T 1/20 (2006.01)
  H04N 5/217 (2011.01)

(52) U.S. Cl.
  CPC ............... G06T 5/50 (2013.01); H04N 5/357 (2013.01); A61B 6/42 (2013.01); A61B 6/52 (2013.01); A61B 6/585 (2013.01); G01T 1/2018 (2013.01); G01T 7/005 (2013.01); H04N 5/2173 (2013.01); H04N 5/32 (2013.01); H04N 5/325 (2013.01); H04N 5/3205 (2013.01); H04N 5/347 (2013.01); H04N 5/378 (2013.01)

(56) References Cited

U.S. PATENT DOCUMENTS

| | | |
|---|---|---|
| 7,386,089 B2 | 6/2008 | Endo et al. |
| 7,476,027 B2 | 1/2009 | Takenaka et al. |
| 7,514,663 B2 | 4/2009 | Yagi et al. |
| 7,532,706 B2 | 5/2009 | Kameshima et al. |
| 7,564,038 B2 | 7/2009 | Endo et al. |
| 7,573,038 B2 | 8/2009 | Yokoyama et al. |
| 7,724,874 B2 | 5/2010 | Kameshima et al. |
| 7,732,778 B2 | 6/2010 | Yokoyama et al. |
| 7,786,448 B2 | 8/2010 | Endo et al. |
| 7,850,367 B2 | 12/2010 | Takenaka et al. |
| 7,994,481 B2 | 8/2011 | Yagi et al. |
| 8,072,514 B2 | 12/2011 | Takenaka et al. |
| 8,093,562 B2 | 1/2012 | Yokoyama et al. |
| 8,167,486 B2 | 5/2012 | Takenaka et al. |
| 8,723,996 B2 | 5/2014 | Yokoyama et al. |
| 2002/0191742 A1 | 12/2002 | Matsuura |
| 2011/0309262 A1 | 12/2011 | Sato et al. |
| 2011/0317054 A1 | 12/2011 | Kameshima et al. |
| 2012/0044392 A1 | 2/2012 | Takenaka et al. |

IMAGING SYSTEM

BACKGROUND OF THE INVENTION

1. Field of the Invention

The present invention relates to an imaging system that is suitably used in a medical diagnosis to take a still image, such as in general radiography, or to take a moving image, such as in fluoroscopy.

2. Description of the Related Art

In recent years, a radiation imaging apparatus using a flat panel detector (hereinafter simply referred to as "detector") that is made of a semiconductor material has come into practical use as an imaging apparatus used in a medical image diagnosis or a nondestructive inspection by radiation. For example, in the medical image diagnosis, such radiation imaging apparatus is used as a digital imaging apparatus to take a still image, such as in general radiography, or to take a moving image, such as in fluoroscopy. As the detector, there is known an indirect-conversion detector obtained by combining a scintillator configured to convert radiation into light with a wavelength band that is detectable by a photoelectric conversion element, and a solid-state imaging element as a sensor for detecting the converted visible light. As the imaging apparatus, for example, for mammography and chest radiography, an imaging apparatus for taking a large-area still image, which uses amorphous silicon (a-Si) of 43 centimeter square at maximum, has been put into practical use.

In this case, the radiation imaging apparatus are desired to achieve technical objects such as high sensitivity, high-speed reading technology, increase in size, and cost reduction. However, amorphous silicon has insufficient semiconductor performance, which makes it difficult to achieve the demand particularly concerning high sensitivity and high-speed reading. In order to cover the shortcomings of the imaging element using amorphous silicon, a configuration including tiled large-area CMOS imaging elements has been put into practical use in recent years.

However, in a related-art amplification-type imaging element such as a CMOS imaging element, radiation may transmit through the scintillator to be exposed to the solid-state imaging element. In this case, there arises a problem in that a noise signal caused by direct incident radiation is superimposed on an image signal generated by the visible light. The noise signal caused by radiation that has directly entered the solid-state imaging element is called blinker noise.

Japanese Patent No. 3894534 discloses a radiation imaging apparatus including a radiation generator and a radiation sensor for converting, into an electrical signal, radiation that has been emitted from the radiation generator toward an object and has transmitted through the object. A signal value of each pixel of the radiation sensor is read twice in a radiation exposure time period. The blinker noise component is extracted as follows. A difference between a first signal of each pixel that is read through first reading in the radiation exposure time period and a second signal of each pixel that is read through second reading performed after the first reading in the radiation exposure time period is calculated, and thus an object component is removed. Then, the first signal is added to the second signal, and an absolute value of the noise component is subtracted from the added value to remove the noise component. In Japanese Patent No. 3894534, the difference between the first signal and the second signal that are read twice in the radiation exposure time period is calculated to remove the object component of the image, and thus the component of blinker noise is extracted. However, in the method of Japanese Patent No. 3894534, unless exactly the same amount of radiation is exposed when reading the first signal and the second signal that are read twice in the radiation exposure time period, when the difference between the first signal and the second signal is calculated, the object component cannot be completely removed, which causes failure in extraction of the blinker noise component. In the actual case, radiation emitted from the radiation generator is not always constant in amount, and always randomly varies. Therefore, it is virtually impossible to control the amount of radiation exposed when reading the first signal and the amount of radiation exposed when reading the second signal to be exactly the same.

SUMMARY OF THE INVENTION

The present invention has an object to provide an imaging system capable of extracting and removing blinker noise with simple processing without a special mechanism. The imaging system according to one embodiment of the present invention includes: a conversion unit configured to convert radiation into light; a plurality of pixels each configured to convert the light converted by the conversion unit into an electrical signal; an extracting unit configured to extract, based on an image formed based on output signals output from the plurality of pixels, a pixel in which noise is generated due to the radiation that has transmitted through the conversion unit to arrive at the plurality of pixels; and a correcting unit configured to perform correction to remove the noise with respect to an output signal output from the pixel extracted by the extracting unit, in which the extracting unit is configured to extract the pixel in which the noise is generated by performing division between a first image and a second image, the first image being formed based on the output signals output from the plurality of pixels in accordance with the radiation exposed to the conversion unit during a first period in a radiation exposure period during which the radiation is exposed to the conversion unit, the second image being formed based on the output signals output from the plurality of pixels in accordance with the radiation exposed to the conversion unit during a second period provided after the first period in the radiation exposure period. The imaging system can extract and remove the blinker noise with simple processing, and the diagnosis performance can be enhanced. Further, the noise can be removed without requiring a special mechanism or member, and hence increase in cost can be suppressed.

Further features of the present invention will become apparent from the following description of exemplary embodiments with reference to the attached drawings.

DESCRIPTION OF THE EMBODIMENTS

First Embodiment

Figure 1:
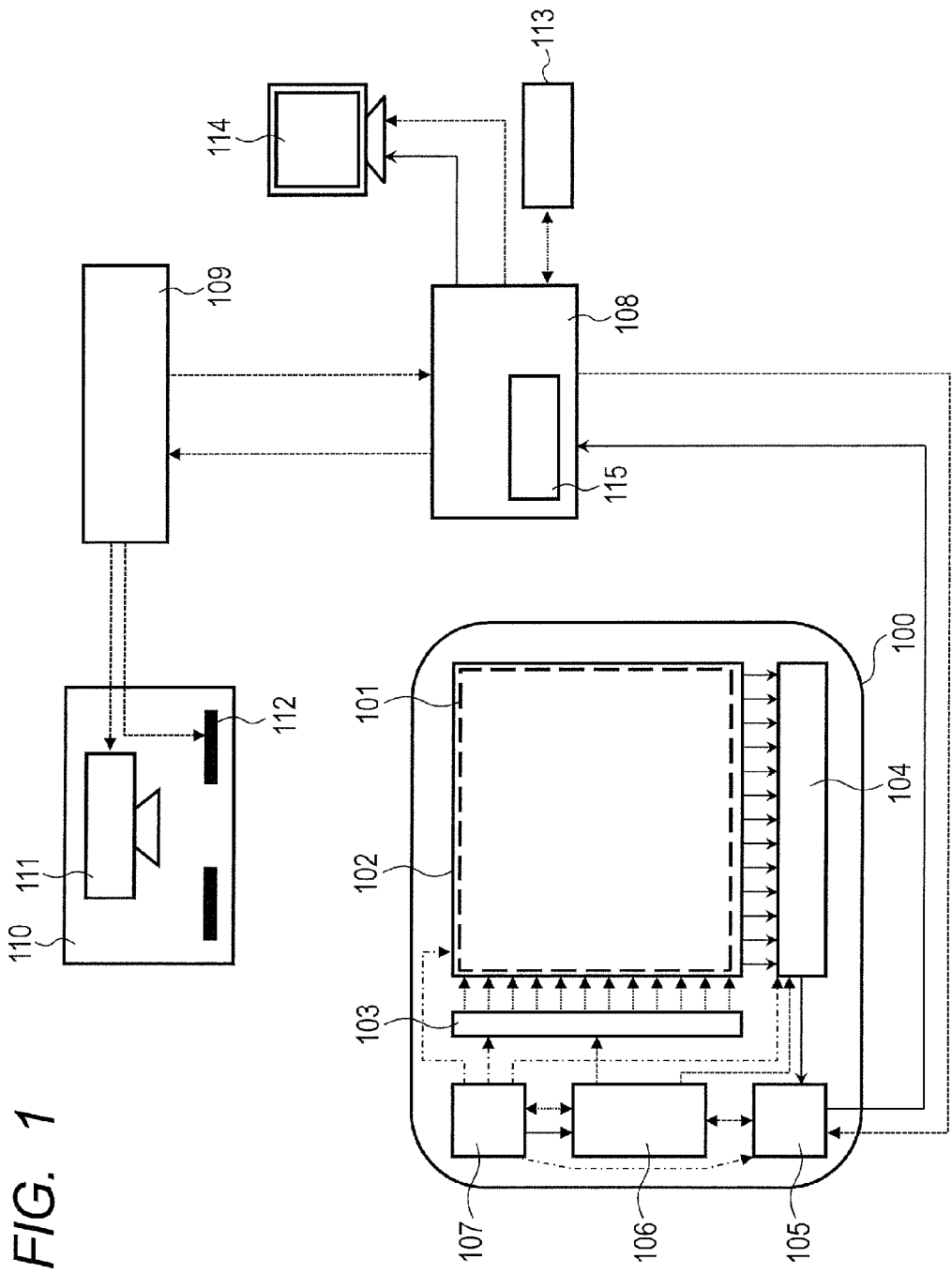
FIG. 1 is a block diagram of an imaging system.

FIG. 1 is a diagram illustrating a configuration example of a radiation imaging system according to a first embodiment of the present invention. The radiation imaging system includes an imaging apparatus 100, a computer 108, a radiation control apparatus 109, a radiation generating apparatus 110, a console 113, and a display apparatus 114. The radiation generating apparatus 110 emits radiation (for example, X-rays). The imaging apparatus 100 includes a scintillator 101, an imaging element 102, a driver circuit 103, a reading circuit 104, a signal processing section 105, a control section 106, and a power supply section 107. The scintillator 101 is a conversion unit configured to convert radiation into light with a wavelength band that is detectable by the imaging element (photoelectric conversion element) 102. The imaging element 102 includes a plurality of pixels each configured to convert light converted by the scintillator 101 into an electrical signal. The driver circuit 103 drives the imaging element 102. The reading circuit 104 outputs the electrical signals from the driven imaging element 102 as image data. The signal processing section 105 processes the image data from the reading circuit 104 and outputs the processed image data. The control section 106 supplies control signals to respective components to control operations of the reading circuit 104 and the driver circuit 103. The power supply section 107 supplies bias voltages to respective components. The signal processing section 105 inputs a control signal from the computer 108 described later, and outputs the control signal to the control section 106. The power supply section 107 includes a regulator for supplying necessary voltages to the scintillator 101, the driver circuit 103, and the reading circuit 104 in response to a voltage from an external power supply or an internal battery (not shown). The computer 108 is configured to input, from the console 113, a control signal for determining radiation exposure conditions, synchronize the radiation control apparatus 109 with the imaging apparatus 100, output an exposure request signal to the radiation control apparatus 109, and output, to the imaging apparatus 100, a control signal for determining the state. Further, the computer 108 incorporates a frame memory 115 for storing image information. The computer 108 performs image arithmetic operation (described later) with respect to image data from the signal processing section 105, and further performs image processing for display and outputs the results to the display apparatus 114. The radiation control apparatus 109 inputs the exposure request signal from the computer 108, and outputs control signals to a radiation source 111 and an exposure limiting mechanism 112. The console 113 outputs, to the computer 108, inputs of radiographing conditions and signals of exposure request as parameters for various controls. The display apparatus 114 displays image data processed by the computer 108.

Figure 2:
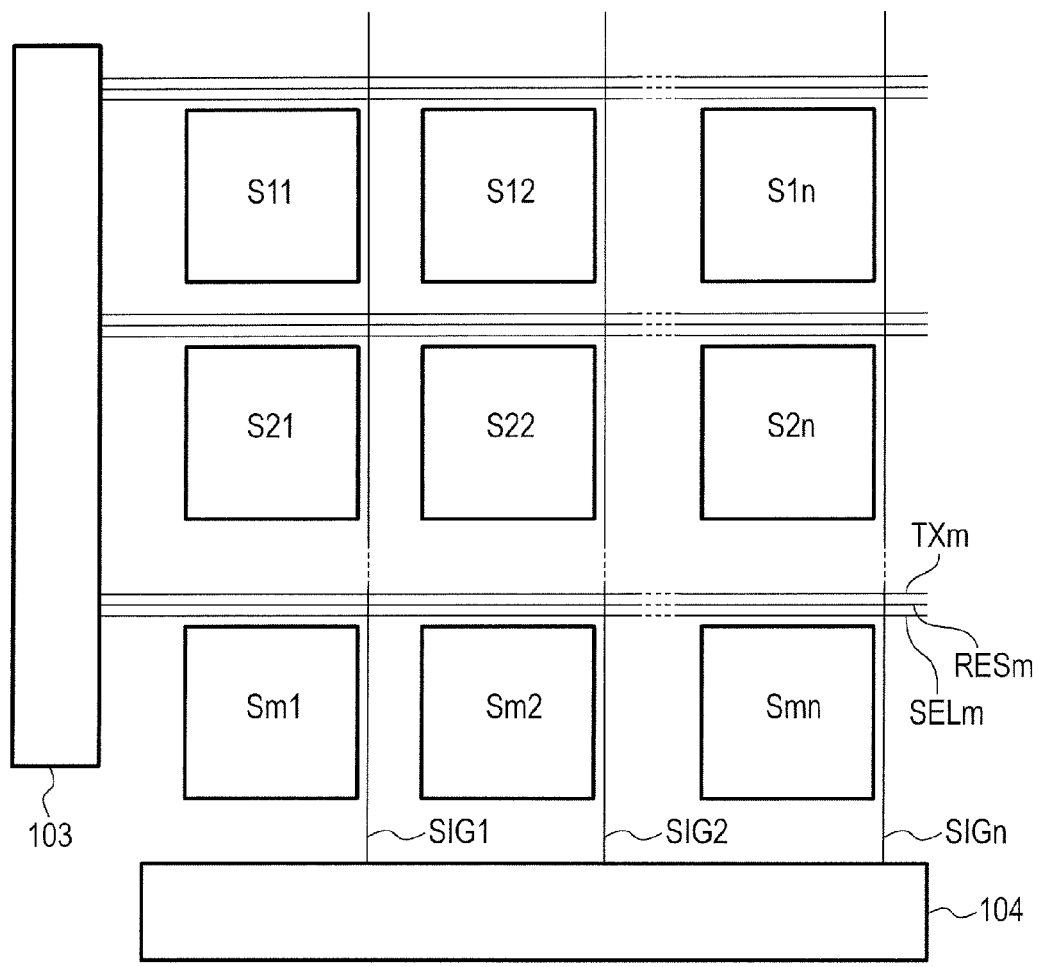
FIG. 2 is a diagram illustrating the entire circuit of an imaging element.
Figure 3:
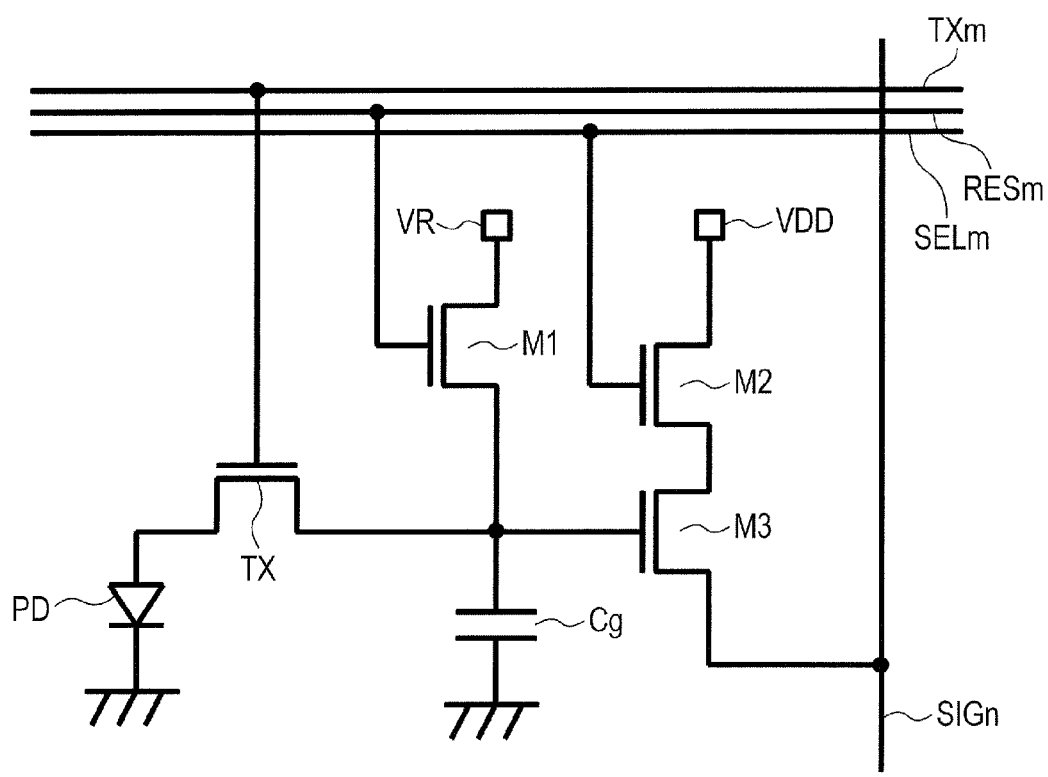
FIG. 3 is a circuit diagram of a single pixel of the imaging element.

Next, with reference to FIGS. 2 and 3, the imaging apparatus 100 of FIG. 1 is described. Note that, in this embodiment, a case where a CMOS solid-state imaging element is used is described. The CMOS solid-state imaging element can be driven with low power consumption, and includes an element for performing photoelectric conversion and an element for driving the element in its vicinity, which are formed inside the same circuit.

FIG. 2 is a diagram illustrating a configuration example of the imaging apparatus 100 of this embodiment. The imaging element 102 includes a plurality of pixels S11 to Smn arranged in matrix. In FIG. 2, the pixels S11 to Smn each represent a pixel arranged in an m-th row and an n-th column. Transfer selection lines TX1 to TXm, reset lines RES1 to RESm, and row selection lines SEL1 to SELm are connected from the driver circuit 103 to the respective pixels S11 to Smn, and supply drive signals for controlling transistors inside the pixels S11 to Smn to the pixels S11 to Smn on a row basis. Further, outputs from the respective pixels S11 to Smn are connected to signal lines SIG1 to SIGn of respective columns. The multiple signal lines SIG1 to SIGn arranged in a column direction output, in parallel, electrical signals output from the plurality of pixels S11 to Smn to the reading circuit 104.

FIG. 3 is a circuit diagram of a single pixel of the imaging element 102. FIG. 3 illustrates a configuration example of the pixel Smn in the m-th row and the n-th column. The remaining pixels also have the same configuration. The pixel Smn includes a photodiode PD, a transfer transistor TX, a capacitor Cg, a reset transistor M1, a row selection transistor M2, and an amplifier transistor M3. The photodiode PD converts incident light into an electrical signal and stores the electrical signal. The transfer transistor TX transfers charges stored in the photodiode PD to the capacitor Cg. The capacitor Cg stores the charges transferred from the photodiode PD. The reset transistor M1 is a reset unit configured to reset the electrical signal stored in the capacitor Cg. The row selection transistor M2 performs row selection of pixels. The amplifier transistor M3 amplifies the charges stored in the capacitor Cg. The photodiode PD has an anode connected to a drain of the transfer transistor TX, and a cathode connected to a ground potential node. The transfer transistor TX has a gate connected to the transfer selection line TXm. The reset transistor M1 has a gate connected to the reset line RESm. The reset transistor M1 has a drain supplied with a reset voltage VR. The row selection transistor M2 has a gate connected to the row selection line SELm. The row selection transistor M2 has a drain connected to a node of a power supply voltage VDD. The amplifier transistor M3 has a source connected to the signal line SIGn.

Figure 4:
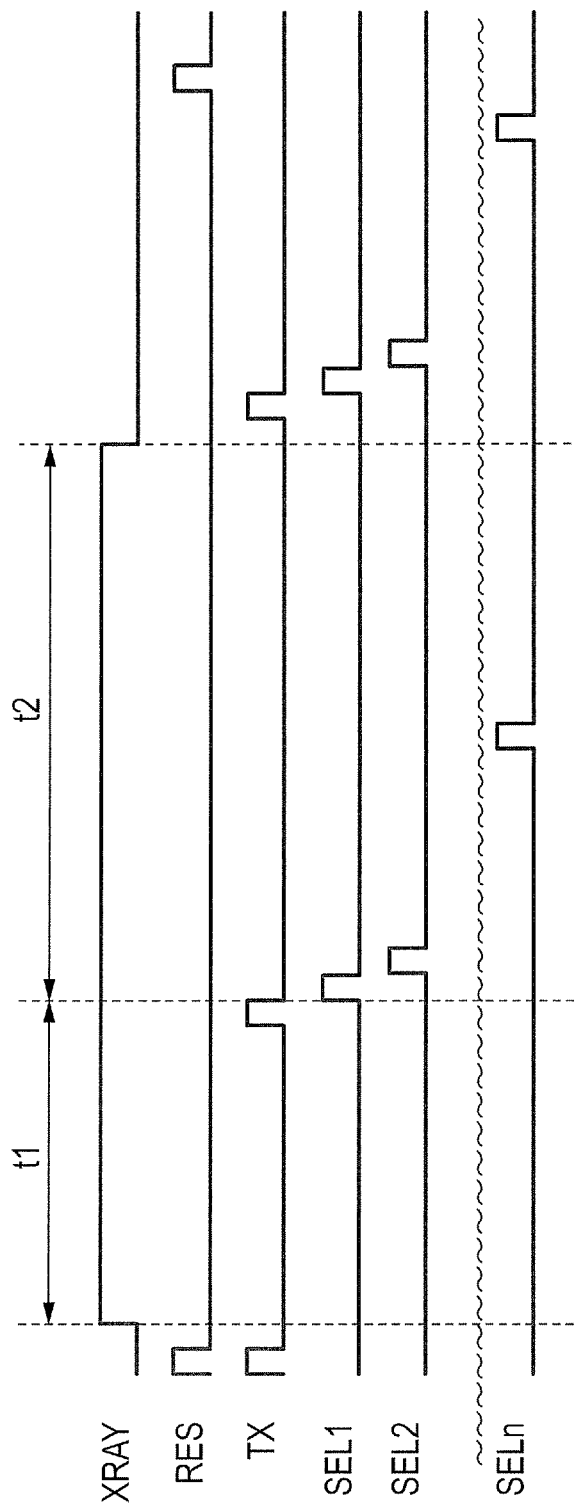
FIG. 4 is a timing chart of a reading operation according to a first embodiment of the present invention.

Next, with reference to FIG. 4, an operation of the imaging apparatus 100 of this embodiment is described. In FIG. 4, a high level in XRAY represents a radiation exposure time period. RES represents a reset pulse of the reset lines RES1 to RESm of FIG. 3. TX represents a transfer pulse of the transfer selection lines TX1 to TXm of FIG. 3. SEL1 to SELn represent row selection pulses of the respective row selection lines SEL1 to SELn.

First, before radiation is exposed, the reset pulse PES and the transfer pulse TX become nigh level to turn on the reset transistors M1 and the transfer transistors TX in all of the pixels. With this, the photodiodes PD and the capacitors Cg in all of the pixels are fixed and reset to the reset voltage VR.

Next, the radiation generating apparatus 110 starts emission of radiation XRAY. The radiation that has transmitted through an object hits the scintillator 101 to be converted into visible light, and after arrival at the imaging element 102, charges corresponding to the light intensity, in other words, charges corresponding to an amount of radiation transmitted through the object are stored in the photodiode PD.

Next, the transfer pulse TX is set to high level at the same time in all of the pixels at an arbitrary time during exposure of radiation XRAY. As a result, the transfer transistors TX are turned on in all of the pixels, and the charges generated through the radiation exposure during a period t1 of FIG. 4 are transferred from the photodiode PD to the capacitor Cg.

Next, the row selection pulses SEL1 to SELn are sequentially set to high level so that the row selection transistors M2 are sequentially turned on for each row. With this, outputs corresponding to the charges transferred to the capacitors Cg are sequentially read to the signal lines SIG1 to SIGn via the amplifier transistors M3 as image data from the first column to the n-th column.

This reading performed after the transfer pulse TX is first set to high level at the same time in all of the pixels is referred to as first reading. An image generated through the first reading is an image of charges generated through radiation during the period t1.

Subsequently, after the exposure of radiation is ended, the transfer pulse TX is set to high level again at the same time in all of the pixels, and charges generated through radiation exposure during a period t2 of FIG. 4 are transferred from the photodiode PD to the capacitor Cg. The charges are added to the charges transferred by the first reading so that charges generated through radiation exposure during a period t1+t2 are stored in the capacitor Cg.

After that, the row selection pulses SEL1 to SELn are sequentially set to high level again, and items of image data from the first column to the n-th column are sequentially read to the signal lines SIG1 to SIGn. This reading performed after the transfer pulse TX is set to high level after the radiation exposure is ended is referred to as final reading. The final reading generates an image of charges generated through the radiation exposure during the entire period t1+t2.

Note that, after the first reading is ended, a reading operation may be further performed once or more in the radiation exposure period t2 before the final reading starts, to thereby acquire three or more images in total. Further, an optimum number of images to be taken may be automatically calculated based on radiation exposure conditions and radiographing conditions. In this embodiment, radiation images are read by the above-mentioned operation.

Figure 5:
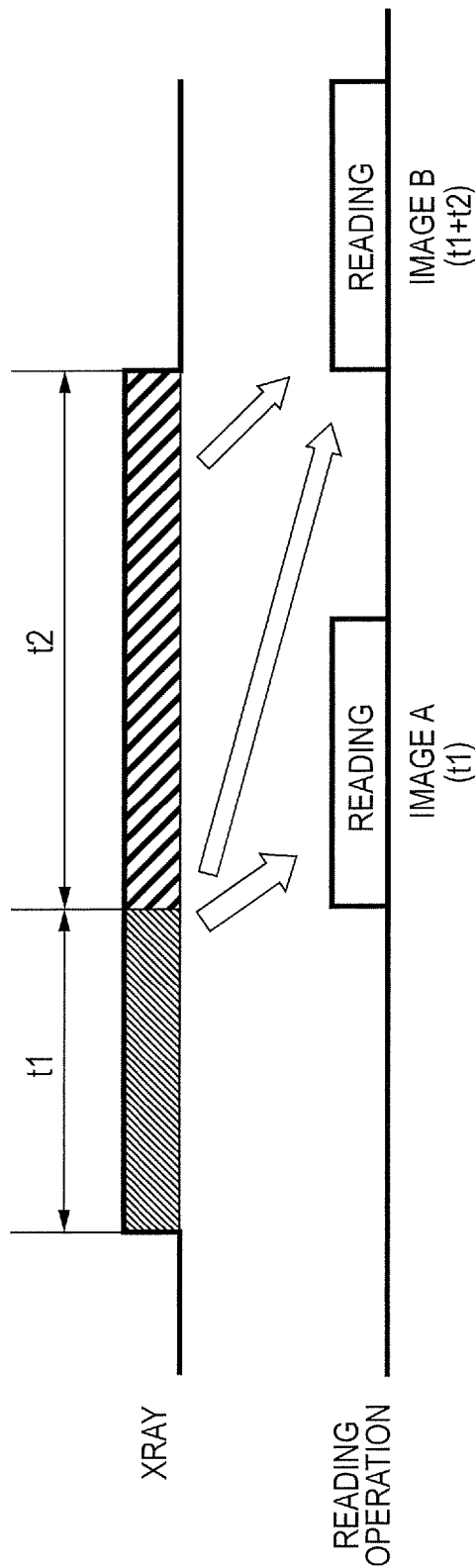
FIG. 5 is a diagram illustrating the reading operation according to the first embodiment.

Subsequently, with reference to FIG. 5, a method of extracting a pixel in which blinker noise is generated and correcting the noise according to this embodiment is described. FIG. 5 simply illustrates the reading operation of FIG. 4. In this embodiment, processing of a case where an image is read once during radiation exposure and an image is read again after the radiation exposure is ended so as to acquire images of two frames in a single radiation exposure is described.

In FIG. 5, a radiation exposure period is set to t1+t2, and through the first reading during the radiation exposure, an image obtained by exposing radiation during the period t1 is read as an image A, which is stored in the frame memory 115 of the computer 108. Then, after the radiation is exposed entirely, the final reading is performed to read an image B as an image obtained by exposing radiation during the period t1+t2, which is stored in the frame memory 115. At this time, blinker noise is generated at random time and place during radiation exposure. That is, blinker noise generated during the period t1 is superimposed on the image A, and blinker noise generated during the period t1+t2 (=entire blinker noise generated during radiation exposure) is superimposed on the image B. Therefore, for example, the computer (extracting unit) 108 performs arithmetic processing using division as the following expression based on the images formed based on the output signals output from the plurality of pixels S11 to Smn. In this manner, a pixel in which noise is generated due to radiation that has transmitted through the scintillator 101 to arrive at the pixels S11 to Smn is extracted.

Image C=Image B/Image A

The image A and the image B are images obtained by imaging the same object in different radiation intensities. In an image C corresponding to quotient of division between those images, all of pixels on which no blinker noise is superimposed have a certain constant value, and thus an image without object information is obtained. A pixel on which blinker noise is superimposed has a pixel value that differs from that of a normal pixel. Therefore, those pixels are distinguishable.

Figure 6:
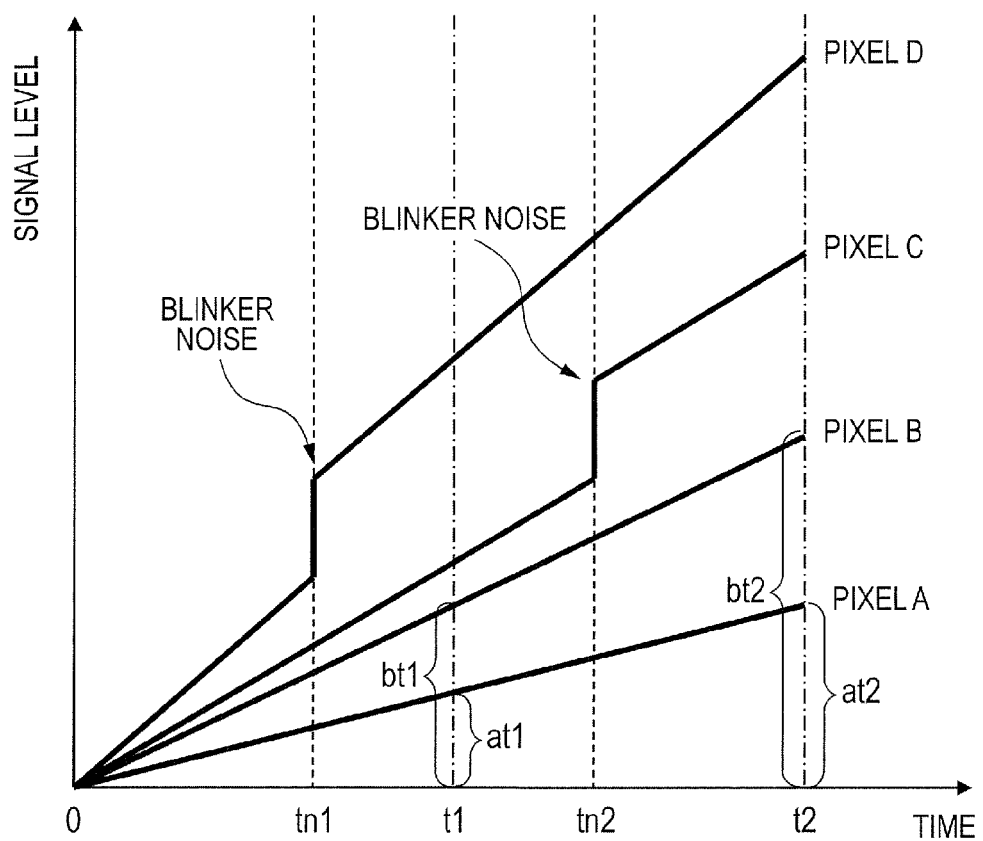
FIG. 6 is a graph showing the principle of extraction of a noise generated pixel.

Now, the principle of extracting a pixel in which blinker noise is generated through arithmetic processing using division is described with reference to FIG. 6. In FIG. 6, a radiation exposure time period is plotted on the horizontal axis, and a pixel signal level is plotted on the vertical axis. FIG. 6 shows changes in signal level of four certain pixels (pixel A, pixel B, pixel C, and pixel D) of the imaging element 102 when radiation is exposed during a time period of from 0 to t2. In this case, the four pixels have different slopes of increase in signal level due to the object, and a part that is liable to transmit the radiation has a large slope, while a part that is less liable to transmit the radiation has a small slope. Further, the pixel A and the pixel B are pixels in which no blinker noise is generated, and the pixel C and the pixel D have blinker noise generated at a timing tn1 and a timing tn2, respectively, at which the signal level increases. In this embodiment, reading is performed once at an arbitrary time during the radiation exposure, and reading is performed again after the radiation exposure. Therefore, the first reading is performed at a timing t1, and radiation exposure is ended at a timing t2. Then, final reading is performed.

In this embodiment, division is performed between the image A acquired at the timing t1 and the image B acquired at the timing t2, to thereby extract the pixel in which the blinker noise is generated. This is equivalent to, in other words, taking a ratio between the signal levels of the two images. When the signal level of the pixel A at the timing t1 is represented by $at1$, the signal level of the pixel B at the timing t1 is represented by $bt1$, the signal level of the pixel A at the timing t2 is represented by $at2$, and the signal level of the pixel B at the timing t2 is represented by $bt2$, the ratio between the signal levels of the two images is $at1/at2$ in the pixel A, and $bt1/bt2$ in the pixel B. Further, based on FIG. 6 and the relationship of triangle similarity, the following expressions are obtained.

$$at1:at2=bt1:bt2$$

$$at1/at2=bt1/bt2$$

This represents that, in other words, by subjecting the two images A and B to arithmetic operation using division, the object information can be removed from the image. Further, the timing t1 is an arbitrary timing between the timing 0 and the timing t2, and hence even when this timing changes, the above-mentioned relationship does not change. Based on the points described above, in the pixels A and B in which no blinker noise is generated, the pixel value becomes a certain constant value when the two images A and B obtained in the embodiment described above are subjected to arithmetic processing using division, and thus the object information can be removed.

Subsequently, a case of a pixel in which the blinker noise is generated is described. Although not illustrated, when the signal level of the pixel C, which corresponds to the pixel in which the blinker noise is generated, at the timing t1 is represented by ct1 and the signal level thereof at the timing t2 is represented by ct2, the following expressions are obtained.

$$at1:at2 \neq ct1:ct2$$

$$at1/at2 \neq ct1/ct2$$

In other words, the pixel C in which the blinker noise is generated has a different pixel value from that of the normal pixel A in which no noise is generated. Further, also in the pixel D in which the blinker noise is generated at a different timing, when the signal level thereof at the timing t1 is represented by dt1 and the signal level thereof at the timing t2 is represented by dt2, the following expression is obtained, which represents that the pixel D has a pixel value different from that of the normal pixel A.

$$at1/at2 \neq dt1/dt2$$

After the reading operation is performed by the above-mentioned drive to acquire the two images A and B, arithmetic processing of division of the two images A and B is performed. In this case, a normal pixel in which no blinker noise is generated has a certain constant value. A pixel in which the blinker noise is generated has a value different from that of the normal pixel, and hence those pixels are distinguishable.

Note that, in order to extract all of the pixels in which the blinker noise is generated, it is necessary to satisfy a requirement that the entire blinker noise is included in any of the images to be subjected to division. In the case of this embodiment, the entire blinker noise is superimposed on the image B, and hence this requirement is satisfied.

Figure 7:
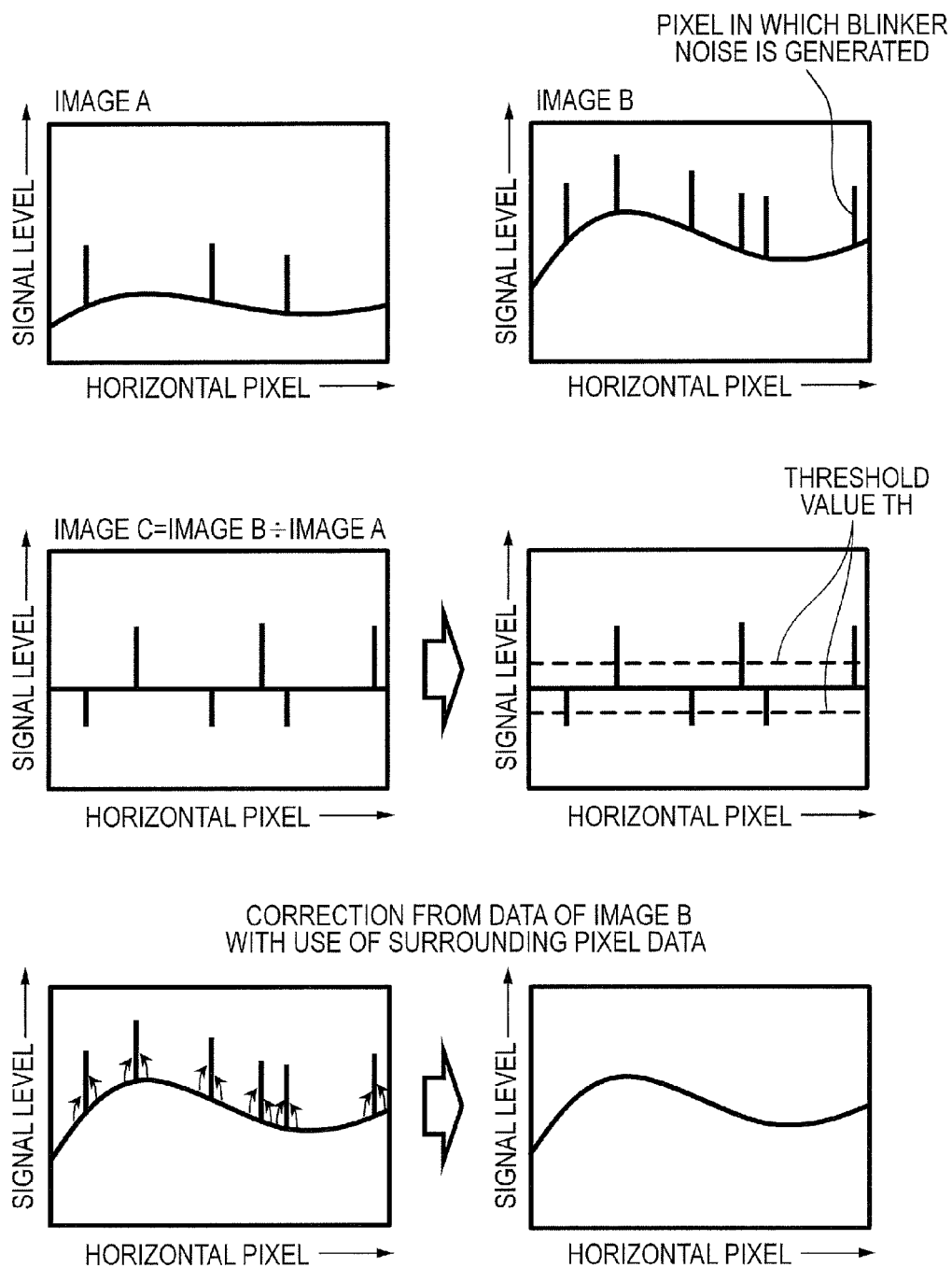
FIG. 7 is a diagram illustrating an example of noise generated pixel extraction and noise removal.

The upper part of FIG. 7 represents the pixel values in a certain row of the image A and the image B obtained through the above-mentioned operation, and represents that the blinker noise is superimposed at some points on the object image to cause increase in signal level. Further, the middle part and the lower part of FIG. 7 represent the process of processing thereafter. In the middle part of FIG. 7, the image C is an image obtained by image B/image A. It is understood that the pixel on which no blinker noise is superimposed has a constant value, but the pixel on which the blinker noise is superimposed has a value different from that of the normal pixel. For example, a threshold value TH as represented in the following expression is provided to the image C subjected to such arithmetic processing, and the coordinates of the pixel that exceeds the threshold value TH are extracted as coordinates of the pixel on which the blinker noise is superimposed.

Threshold value TH=(average value of image C)± (average value of image C)×10%)

Note that, the above-mentioned percentage value normally ranges from about 3% to about 20%. The threshold value TH is determined based on the required quality, and it is preferred to set the threshold value within an allowable range equivalent to an allowable range of an error due to fluctuations of the imaging element 102. Normally, the imaging element 102 has fluctuations in linearity or the like, and an error is allowed within a certain range. For example, when the error due to the fluctuations of the imaging element 102 is allowed in a range of 10%, it is considered that, in the image C subjected to division processing, the value of the normal pixel on which no blinker noise is superimposed has the maximum error of 10%. Therefore, it is preferred to also set the threshold value of the blinker noise in a manner that an error equivalent thereto is allowed. Note that, the threshold value in the positive direction may be different from the threshold value in the negative direction with respect to the average value. Further, in the above, the threshold value is set with use of the average value of the image, but, for example, the threshold value may be defined as five times the standard deviation of the image C. Further, the setting value of the threshold value may be automatically changed based on the output value of the image. In any of the cases, it is required that the blinker noise not be recognized in the diagnosis image.

As described above, the computer (extracting unit) 108 acquires the first image A based on the output signals output from the plurality of pixels S11 to Smn in accordance with the radiation exposed to the scintillator (conversion unit) 101 during the first period t1 of the radiation exposure period during which the radiation is exposed to the scintillator (conversion unit) 101. Then, the computer (extracting unit) 108 acquires the second image B based on the output signals output from the plurality of pixels S11 to Smn in accordance with the radiation exposed to the scintillator (conversion unit) 101 during the second period t2 provided after the first period t1 in the radiation exposure period. Then, the computer (extracting unit) 108 performs division between the first image A and the second image B to extract the pixel in which noise is generated.

After extracting the pixel in which the noise is generated, as shown in the lower part of FIG. 7, the computer (correcting unit) 108 performs correction to remove the noise with respect to the output signal output from the pixel extracted as noise coordinates from the image B. For example, the correction is performed by once cancelling the original pixel value of the pixel having the coordinates that are extracted as the pixel on which the blinker noise is superimposed, and setting the average value of the adjacent pixel as its pixel value. As described above, according to this embodiment, a good-quality image with small noise can be obtained.

Second Embodiment

An imaging apparatus according to a second embodiment of the present invention has a configuration similar to that in the first embodiment illustrated in FIGS. 1, 2, and 3, and hence detailed description thereof is omitted herein. This embodiment differs from the first embodiment in that the reading operation is performed twice or more during the radiation exposure and once or more after the exposure. Thus, this embodiment refers to a processing method when three or more images are acquired.

Figure 8:
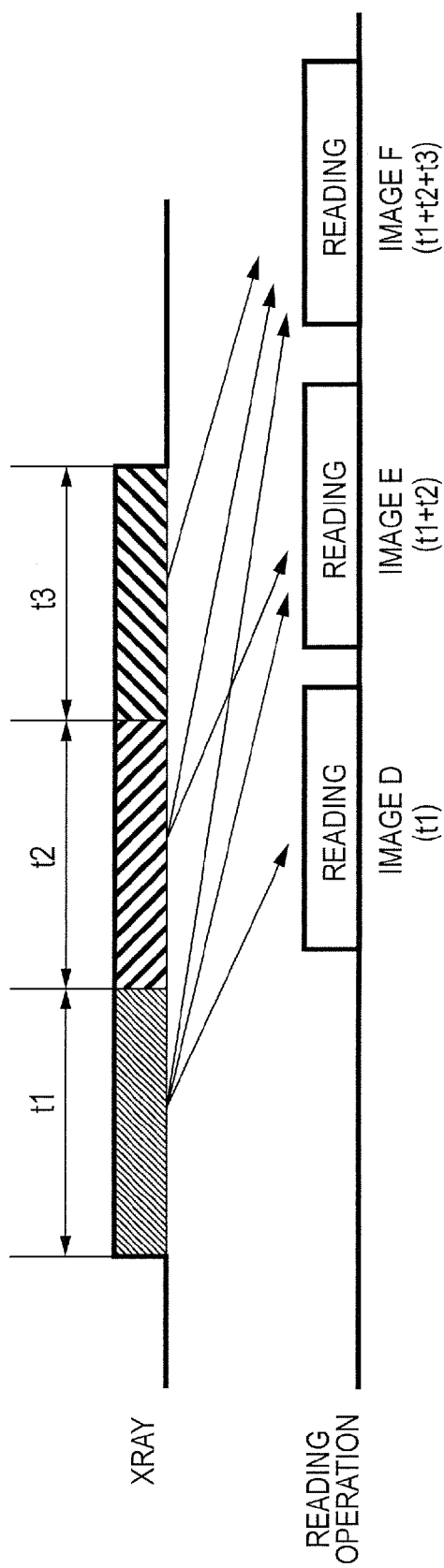
FIG. 8 is a diagram illustrating a reading operation according to a second embodiment of the present invention.

FIG. 8 simply illustrates the reading operation when the image is read three times in a single radiation exposure. In FIG. 8, the radiation exposure period is set to t1+t2+t3, and through first reading during the radiation exposure, an image of charges generated through the radiation exposure during the period t1 is read as an image D. Next, through second reading during the radiation exposure, an image of charges generated through the radiation exposure during the period t1+t2 is read as an image E. Finally, after the radiation is entirely exposed, through final reading, an image of charges generated through the radiation exposure during a period t1+t2+t3 is read as an image F, and the images D, E, and F are stored in the frame memory 115.

Figure 9:
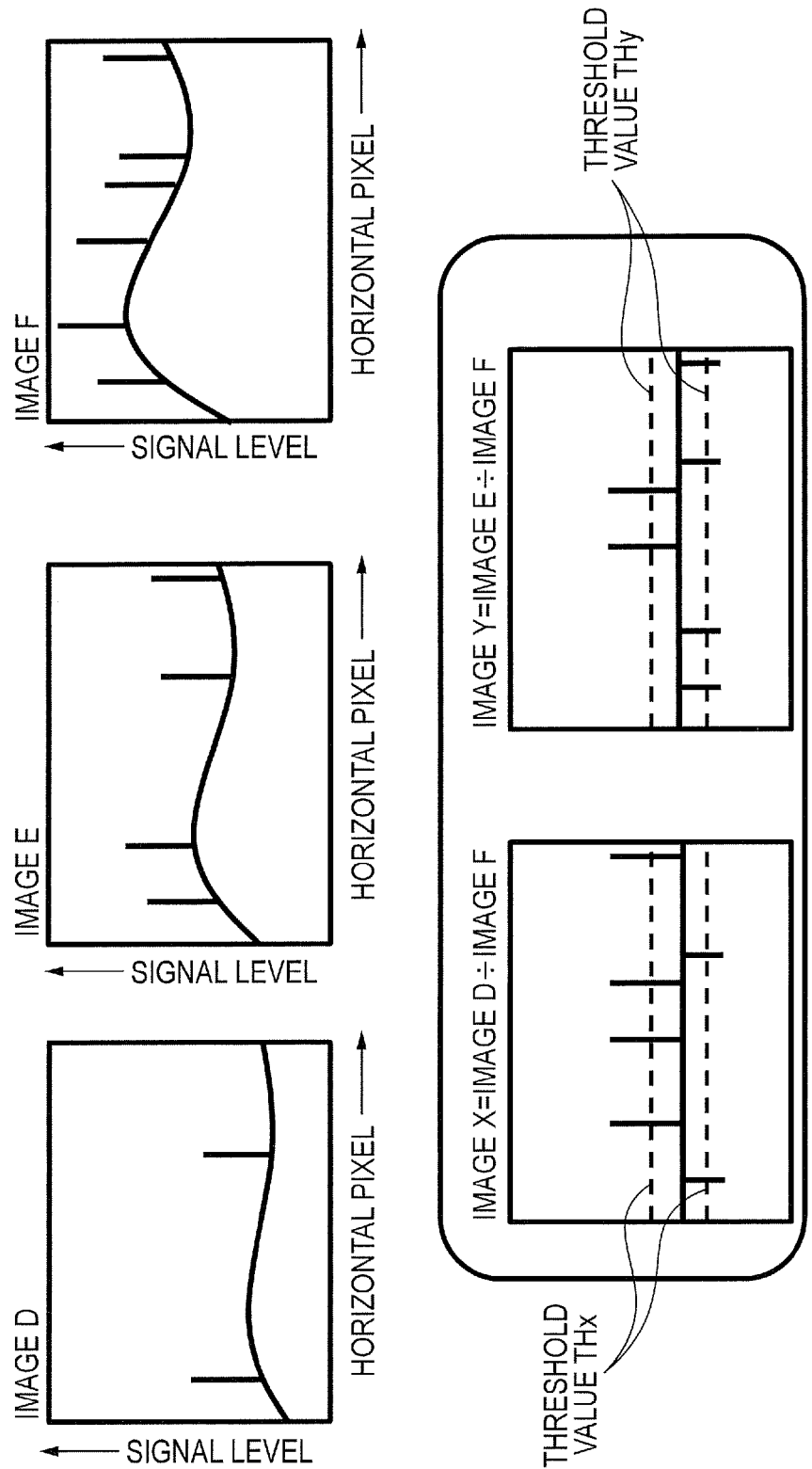
FIG. 9 is an explanatory diagram of noise generated pixel extraction according to the second embodiment.

Next, with reference to FIG. 9, a method of extracting the pixel in which the blinker noise is generated is described. FIG. 9 represents pixel values in a certain row of the image D, the image E, and the image F, and represents the images read in this embodiment and the method of extracting the pixel in which the blinker noise is generated with use of the images. In this embodiment, for example, images X and Y are obtained through arithmetic processing using division as the following expressions to extract the pixel in which the noise is generated.

Image $X$=Image $D$/Image $F$

Image $Y$=Image $E$/Image $F$

Also in this embodiment, similarly to the first embodiment, in the image X and the image Y, all of the normal pixels on which no blinker noise is superimposed have a certain constant value, and the pixel on which the blinker noise is superimposed takes a value after arithmetic operation that is different from a normal pixel value. In this embodiment, similarly to the first embodiment, for example, threshold values THx and THy as the following expressions are provided. In the images X and Y, coordinates of the pixels that exceed the threshold values Tx and Ty, respectively, are extracted as coordinates of the pixel on which the blinker noise is superimposed. The preferred setting value of the threshold value is similar to that in the first embodiment, and hence detailed description thereof is omitted herein.

Threshold value TH$x$=(average value of image $X$)±{(average value of image $X$)×10%}

Threshold value TH$y$=(average value of image $Y$)±{(average value of image $Y$)×10%}

Further, the logical conjunction of the coordinates extracted from the image X and the coordinates extracted from the image Y is taken, and the coordinates having the value of this logical conjunction of 1 are set as coordinates of the pixel in which the blinker noise is generated. From the three or more images acquired as described above, two or more images subjected to arithmetic processing are created to extract the coordinates of the pixel in which the blinker noise is generated. Then, the logical conjunction or the logical disjunction of the extracted coordinates is taken. With this, the coordinate extraction error due to a noise component other than the blinker noise can be reduced, and the extraction accuracy of the coordinates of the pixel in which the blinker noise is generated can be increased.

Note that, there are many calculation expressions for extracting the pixel in which the blinker noise is generated other than the method of this embodiment. In order to extract all of the pixels in which the blinker noise is generated, it is necessary to satisfy the requirement that the entire blinker noise is included in any of the images to be subjected to division.

As described above, the computer (extracting unit) 108 acquires the first image D based on the output signals output from the plurality of pixels S11 to Smn in accordance with the radiation exposed to the scintillator (conversion unit) 101 during the first period t1 of the radiation exposure period during which the radiation is exposed to the scintillator (conversion unit) 101. Then, the computer (extracting unit) 108 acquires the third image E based on the output signals output from the plurality of pixels S11 to Smn in accordance with the radiation exposed to the scintillator (conversion unit) 101 during the third period t2 provided after the first period t1 and before the second period t3 in the radiation exposure period. Then, the computer (extracting unit) 108 acquires the second image F based on the output signals output from the plurality of pixels S11 to Smn in accordance with the radiation exposed to the scintillator (conversion unit) 101 during the second period t3 provided after the third period t2 in the radiation exposure period. Then, the computer (extracting unit) 108 performs division between the first image D and the second image F, and performs division between the third image E and the second image F. Then, the computer (extracting unit) 108 performs logical operation with use of the image X as a result of the division between the first image D and the second image F and the image Y as a result of the division between the third image E and the second image F. In this manner, the pixel in which the noise is generated is extracted.

Third Embodiment

In a third embodiment of the present invention, a method of performing reading by a method that does not leave an electrical signal inside the pixel after the reading processing, and an arithmetic processing method of a case where the reading is performed by this method are described with reference to FIGS. 10, 11, and 12. In the first embodiment (FIGS. 4 and 5), the reset transistor M1 does not reset the plurality of pixels S11 to Smn in a period after the first image A is output in accordance with the radiation during the first period t1 and before the second image b is output in accordance with the radiation during the second period t2. Further, in the second embodiment (FIG. 8), the reset transistor M1 does not reset the plurality of pixels S11 to Smn in a period after the first image D is output in accordance with the radiation during the first period t1 and before the second image F is output in accordance with the radiation during the second period t3. In contrast, in the third embodiment (FIGS. 10 and 11), the reset transistor M1 resets the plurality of pixels S11 to Smn in a period after a first image G is output in accordance with the radiation during the first period t1 and before a second image H is output in accordance with the radiation during the second period t2. Note that, an imaging apparatus according to the third embodiment has a similar configuration to that in the first and second embodiments illustrated in FIGS. 1, 2, and 3, and hence detailed description thereof is omitted herein.

Figure 10:
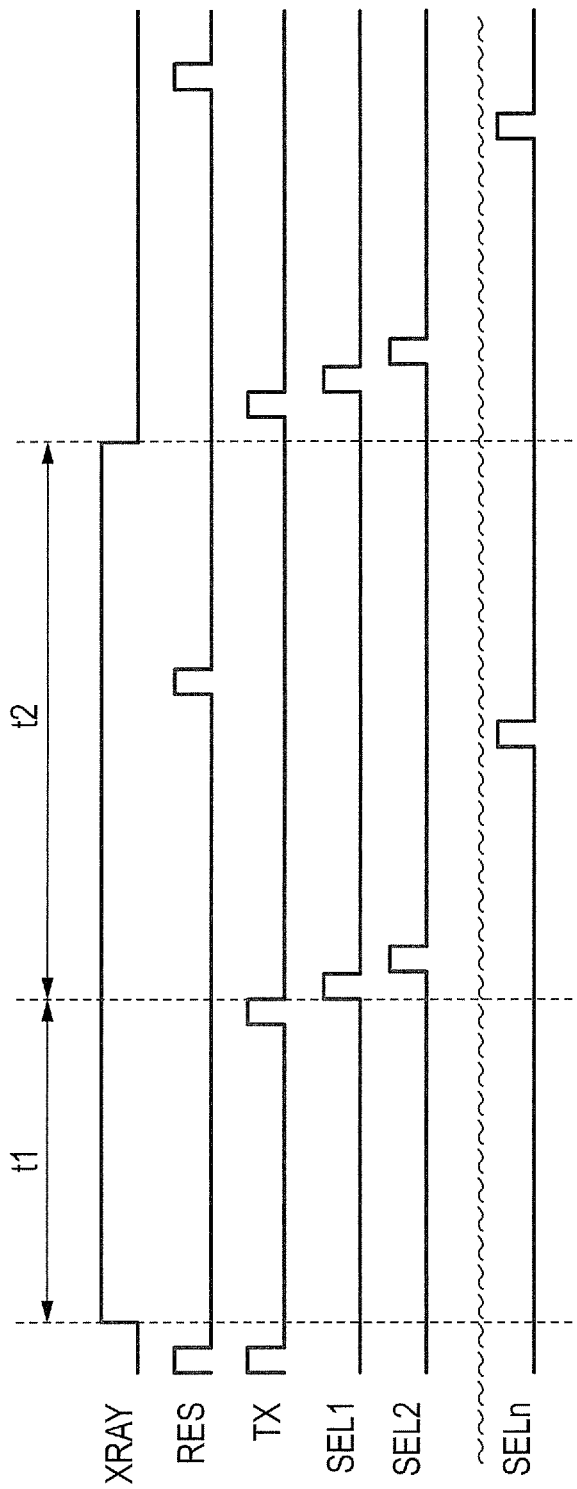
FIG. 10 is a timing chart of a reading operation according to a third embodiment of the present invention.
Figure 11:
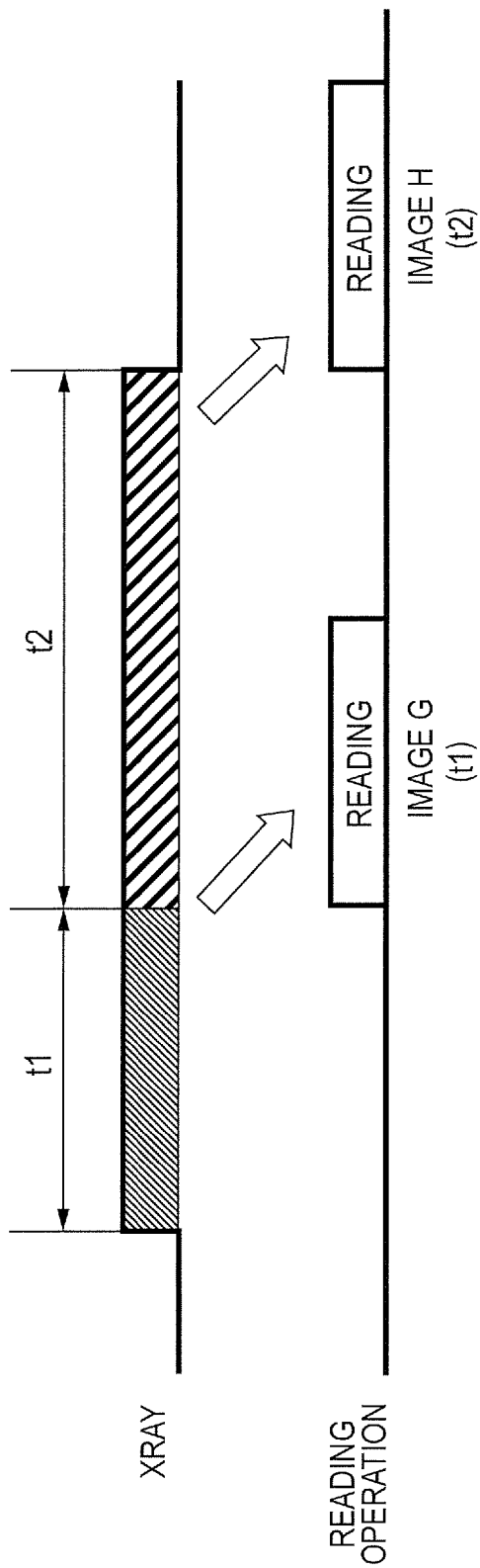
FIG. 11 is a diagram illustrating a reading operation according to the third embodiment.

Now, with reference to FIG. 10, a point different from the first embodiment in a reading operation in the imaging apparatus 100 of the third embodiment is described. In FIG. 10, a high level in XRAY represents a radiation exposure time period. RES represents a reset pulse of the reset lines RES1 to RESm of FIG. 3. TX represents a transfer pulse of the transfer selection lines TX1 to TXm of FIG. 3. SEL1 to SELn represent row selection pulses of the row selection lines SEL1 to SELn.

The operation is similar to that in the first embodiment until the period t1 in FIG. 10 ends, and first, the first reading is performed during the radiation exposure. The image generated through the first reading is an image of charges generated through the radiation exposure during the period t1.

Next, after the first reading is ended and during the radiation exposure, the reset pulse RES is once set to high level to reset the charges of the capacitor Cg. Subsequently, after the radiation exposure is ended, the transfer pulse TX is set to high level at the same time in all of the pixels so that the charges generated through the radiation exposure during the period t2 of FIG. 10 are transferred from the photodiode PD to the capacitor Cg. Thus, the charges generated through the radiation exposure during the period t2 are transferred to the capacitor Cg. After that, similarly to the first embodiment, the final reading is performed. In the third embodiment, the image generated through the final reading is an image of charges generated through the radiation exposure during the period t2.

Note that, after the first reading is ended, a reading operation may be further performed once or more during the radiation exposure period before the final reading starts, to thereby acquire three or more images in total. Further, an optimum number of images to be taken may be automatically calculated based on radiation exposure conditions and radiographing conditions similarly to the first embodiment.

Subsequently, with reference to FIG. 11, a different point, from the first embodiment, of a method of correcting blinker noise generated in a pixel according to the third embodiment is described. FIG. 11 simply illustrates the reading operation. In this embodiment, processing of a case where an image is read once during radiation exposure and an image is read again after the radiation exposure is ended so as to acquire images of two frames in a single radiation exposure is described. In the third embodiment, through the first reading during the radiation exposure, an image obtained by exposing radiation during the period t1 is read as the image G, which is stored in the frame memory 115 of the computer 108. Then, after the radiation is entirely exposed, the final reading is performed to read an image obtained by exposing radiation during the period t2 as the image H, which is stored in the frame memory 115.

At this time, the blinker noise is generated at random time and place during radiation exposure. That is, the blinker noise generated during the period t1 is superimposed on the image G, and the blinker noise generated during the period t2 is superimposed on the image H. Therefore, in this embodiment, arithmetic processing using division as the following expression is performed to obtain an image Z, for example. In this manner, a pixel in which noise is generated is extracted.

Image $Z$=Image $H$/Image $G$

Similarly to the first embodiment, in the image Z, all of the pixels in which no blinker noise is superimposed have a certain constant value, and hence an image without object information is obtained. The pixel on which the blinker noise is superimposed has a pixel value different from a normal pixel value, and hence those pixels are distinguishable. Note that, in order to extract all of the pixels in which the blinker noise is generated, it is necessary to satisfy the requirement that, similarly to the first embodiment, the entire blinker noise is included in any of the images to be subjected to division.

In the third embodiment, the entire blinker noise is generated during the period t1+t2. The blinker noise generated during the period t1 is superimposed on the image G, and the blinker noise generated during the period t2 is superimposed on the image H. Therefore, the above-mentioned requirement is satisfied.

Figure 12:
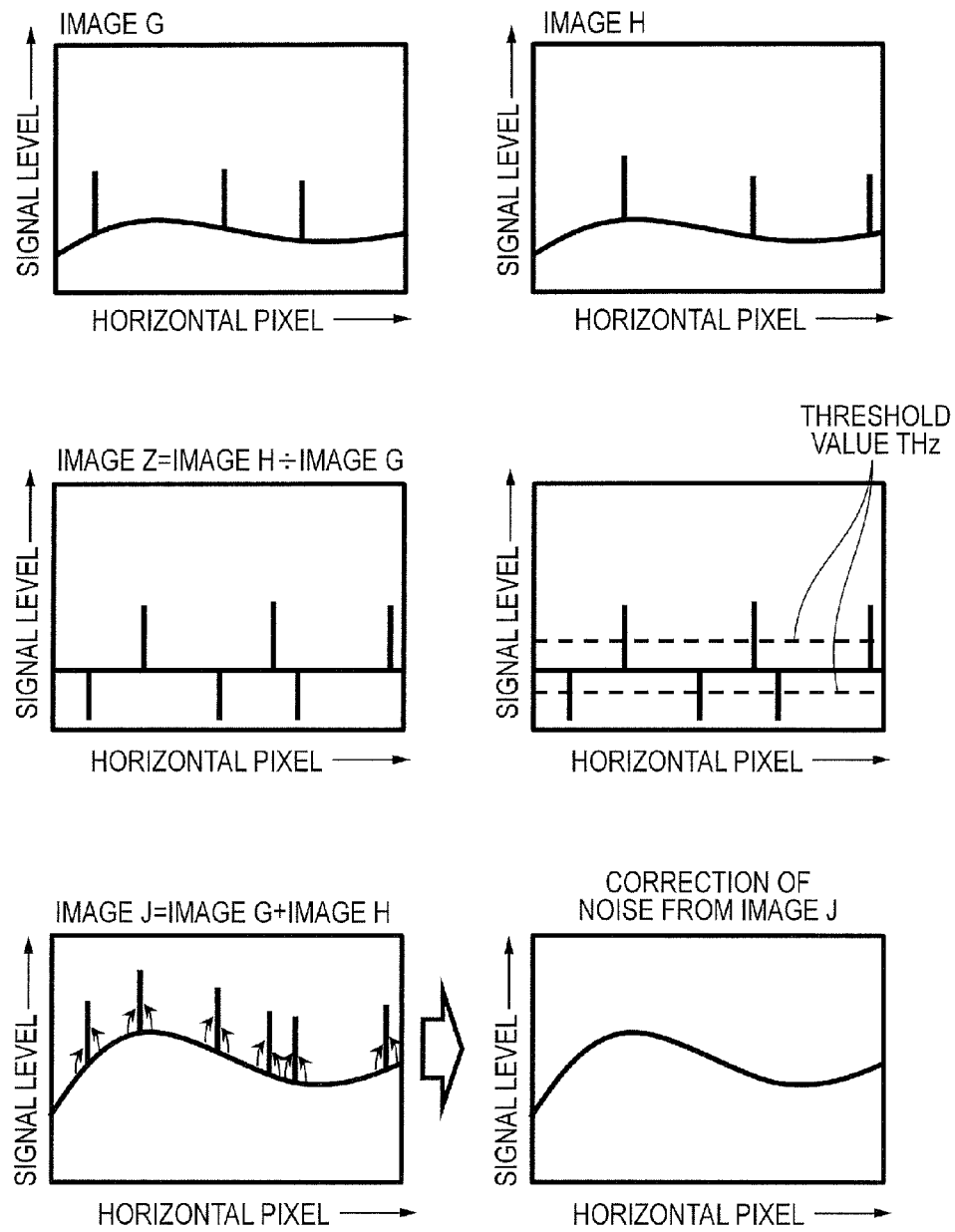
FIG. 12 is a diagram illustrating an example of noise generated pixel extraction and noise removal.

The upper part of FIG. 12 represents the pixel values in a certain row of the image G and the image H, and represents that the blinker noise is superimposed at some points on the object image to cause increase in signal level. The middle part and the lower part of FIG. 12 represent the process of processing thereafter. In the middle part of FIG. 12, the image Z is obtained through arithmetic operation of image H/image G. It is understood that the pixel on which no blinker noise is superimposed has a constant value, but the pixel on which the blinker noise is superimposed has a value different from that of the normal pixel. For example, a threshold value THz as represented in the following expression is provided to the image Z subjected to such arithmetic processing, and the coordinates of the pixel that exceeds the threshold value THz are extracted as coordinates of the pixel on which the blinker noise is superimposed. The preferred setting value of the threshold value is similar to that in the first embodiment, and hence detailed description thereof is omitted herein.

Threshold value TH$z$=(average value of image $Z$)±{(average value of image $Z$)×10%}

Subsequently, correction is performed to remove the blinker noise based on the extracted coordinate information. In the third embodiment, the image G is an image of charges generated through the radiation exposure during the period t1, and the image H is an image of charges generated through the radiation exposure during the period t2. An image of charges generated through the radiation exposure during the period t1+t2 is not acquired. Therefore, an image J is obtained by the following expression.

Image $J$=Image $G$+Image $H$

The image J is an image of charges generated through the radiation exposure during the period t1+t2, and the image J is used to perform correction so as to remove the blinker noise. The correction is performed in the pixel having coordinates extracted as the pixel on which the blinker noise is superimposed by once cancelling the original pixel value of the image J, and setting, for example, an average value of the adjacent pixel as its pixel value.

Next, another method of extracting the pixel in which the noise is generated is described. When the images acquired during the radiation exposure are represented by $m_1$, $m_2$, $m_3$ . . . , and $m_{n-1}$, and the image acquired after the radiation exposure is ended is represented by $m_n$ (n is an integer), multiple fifth images are acquired through arithmetic operation of the following expression (1). That is, the computer (extracting unit) 108 acquires a fourth image by adding the first images $m_1$, $m_2$, $m_3$ . . . , and $m_{n-1}$ and the second image $m_n$. Then, with use of the result of division between the first images $m_1$, $m_2$, $m_3$ . . . , and $m_{n-1}$ and the fourth image and the result of division between the second image $m_n$ and the fourth image, the multiple fifth images are acquired as the expression (1).

$$m_1 \div \sum_{k=1}^{n} m_k \qquad (1)$$

$$m_2 \div \sum_{k=1}^{n} m_k$$

$$\vdots$$

$$m_n \div \sum_{k=1}^{n} m_k$$

After that, with respect to the multiple images acquired through the expression (1), similarly to the second embodiment (FIG. 9), with use of the threshold values THx and THy or the like, the image in which the noise is generated is extracted. The correction method thereafter is similar to that in the second embodiment. That is, the extracting unit performs logical operation (logical conjunction or logical disjunction) of the multiple fifth images of the expression (1) to extract the pixel in which the noise is generated.

Fourth Embodiment

As described in the second embodiment, by increasing the number of times of acquiring an image during the radiation exposure period, the extraction accuracy of the pixel in which the blinker noise is generated can be increased. However, a time period necessary for the reading operation is predetermined, and hence when the radiation exposure time period is short, for example, the number of times of acquiring an image cannot be needlessly increased. When the radiation exposure time period is long, the number of times of acquiring an image can be increased. However, when the number of times of acquiring an image is needlessly increased, power consumption increases, which may cause a higher risk of malfunction or the like due to heat generation. In the case of an imaging apparatus of a type that is driven by a battery, the total number of images to be taken may be reduced. Therefore, there is a limit in the number of times of acquiring an image.

Further, there is a relationship between the intensity of radiation and the probability of occurrence of the blinker noise, and, for example, it is understood that the probability of occurrence of the blinker noise is low when the tube voltage of the radiation source 111 is high. Therefore, in a fourth embodiment of the present invention, a method of automatically defining the number of times of acquiring an image during the radiation exposure based on those pieces of information is described with reference to FIG. 1.

An operator inputs, to the console 113, information such as imaging conditions of the radiation source 111 (tube voltage and tube current of radiation), radiation exposure conditions (exposure time period), and/or power consumption. Those pieces of information are output to the computer 108. Based on those pieces of information, the computer 108 calculates the number of images that are required to be taken to completely extract the pixels in which the blinker noise is generated based on the information on the imaging conditions, the maximum number of images that can be taken based on the radiation exposure conditions, and the limitation number of images to be taken that is determined based on the relationship of power consumption and the like. Then, the computer 108 compares those items to determine the minimum number as the number of times of acquiring an image during the radiation exposure. After that, the computer 108 synchronizes the radiation control apparatus 109 with the imaging apparatus 100, outputs the exposure request signal to the radiation control apparatus 109, and outputs the control signal for determining the operation of the imaging apparatus 100, to thereby start the operation. The drive performed during and after the radiation exposure, the arithmetic method for extracting the coordinates of the pixel with noise, and the noise correcting method are similar to those in the first to third embodiments.

According to the first to fourth embodiments, it is possible to extract and remove the blinker noise with simple processing, and the diagnosis performance can be enhanced. Further, the noise can be removed without requiring a special mechanism or member, and hence increase in cost can be suppressed.

Note that, the above-mentioned embodiments are all merely specific examples for embodying the present invention, and the technical range of the present invention may not be interpreted in a limited way by those embodiments. That is, the present invention may be embodied in various modes without departing from the technical idea or main features thereof.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-056877, filed Mar. 19, 2013, which is hereby incorporated by reference herein in its entirety.

What is claimed is:

1. An X-ray radiation imaging system comprising:
a conversion unit configured to convert x-ray radiation into light;
a plurality of pixels each configured to convert the light converted by the conversion unit into an electrical signal;
an extracting unit configured to extract, based on an image formed based on output signals output from the plurality of pixels, a pixel in which noise is generated due to the radiation that has transmitted through the conversion unit to arrive at the plurality of pixels; and
a correcting unit configured to perform correction to remove the noise with respect to an output signal output from the pixel extracted by the extracting unit,
wherein the extracting unit is configured to extract the pixel in which the noise is generated by performing division between a first image and a second image, the first image being formed based on the output signals output from the plurality of pixels in accordance with the x-ray radiation exposed to the conversion unit during a first period in an x-ray radiation exposure period during which the x-ray radiation is exposed to the conversion unit, the second image being formed based on the output signals output from the plurality of pixels in accordance with the x-ray radiation exposed to the conversion unit during a second period provided after the first period in an x-ray radiation exposure period.

2. The X-ray radiation imaging system according to claim 1, wherein the extracting unit is configured to extract the pixel in which the noise is generated by further performing division between a third image and the second image, the third image being formed based on the output signals output from the plurality of pixels in accordance with the x-ray radiation exposed to the conversion unit during a third period provided after the first period and before the second period in the x-ray radiation exposure period, and further performing logical operation with use of a result of the division between the first image and the second image and a result of the division between the third image and the second image.

3. The X-ray radiation imaging system according to claim 1, further comprising a reset unit configured to reset the electrical signal stored in each of the plurality of pixels,
wherein the reset unit avoids resetting the plurality of pixels in a period after the output signals are output from the plurality of pixels in accordance with the x-ray radiation exposed during the first period and before the output signals are output from the plurality of pixels in accordance with the x-ray radiation exposed during the second period.

4. The X-ray radiation imaging system according to claim 3, wherein the correcting unit is configured to perform the correction based on the second image.

5. The X-ray radiation imaging system according to claim 1, further comprising a reset unit configured to reset the electrical signal stored in each of the plurality of pixels, wherein the reset unit resets the plurality of pixels in a period after the output signals are output from the plurality of pixels in accordance with the x-ray radiation exposed during the first period and before the output signals are output from the plurality of pixels in accordance with the x-ray radiation exposed during the second period.

6. The X-ray radiation imaging system according to claim 5, wherein the correcting unit is configured to perform the correction based on the first image and the second image.

7. The X-ray radiation imaging system according to claim 5, wherein the extracting unit is configured to extract the pixel in which the noise is generated by adding the first image to the second image to acquire a fourth image, and performing logical operation with use of a result of division between the first image and the fourth image and a result of division between the second image and the fourth image.

8. The X-ray radiation imaging system according to claim 1, wherein a number of times of acquiring an image during the x-ray radiation exposure period is determined based on at least one of an imaging condition, an x-ray radiation exposure condition, or power consumption.

9. The X-ray radiation imaging system according to claim 1, further comprising an x-ray radiation generating apparatus configured to emit x-ray radiation.

* * * * *